(12) United States Patent  
Peterson et al.

(10) Patent No.: US 6,783,976 B2  
(45) Date of Patent: Aug. 31, 2004

(54) CARRIER AND SPECIMEN-HANDLING TOOL FOR USE IN DIAGNOSTIC TESTING

(75) Inventors: Kristy Peterson, Salt Lake City, UT (US); Donald J. McMichael, South Jordan, UT (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 209 days.

(21) Appl. No.: 10/026,200

(22) Filed: Dec. 21, 2001

(65) Prior Publication Data

US 2003/0119181 A1 Jun. 26, 2003

(51) Int. Cl.$^7$ .................................................. C12M 1/26
(52) U.S. Cl. ....................... 435/309.1; 600/210; 600/214
(58) Field of Search ........................... 435/283.1, 309.1, 435/309.3, 810; 600/210, 214

(56) References Cited

U.S. PATENT DOCUMENTS

| | | |
|---|---|---|
| 1,521,689 A | 1/1925 | King |
| 3,145,086 A | 8/1964 | Free et al. |
| 3,395,082 A | 7/1968 | Mast |
| 3,411,723 A | 11/1968 | Kohn |
| 3,461,036 A | 8/1969 | Harvill et al. |
| 3,653,389 A | 4/1972 | Shannon .................... 128/354 |
| 3,828,765 A | 8/1974 | McDonald |
| 3,873,269 A | 3/1975 | Kraffczyk et al. |
| D241,803 S | 10/1976 | Amiot |
| 4,016,268 A | 4/1977 | Goldenberg et al. ........ 424/231 |
| 4,016,865 A | 4/1977 | Fredricks |
| 4,027,658 A | 6/1977 | Marshall |
| 4,101,382 A | 7/1978 | Chang |
| D249,772 S | 10/1978 | Amiot ............................ D8/3 |
| 4,132,502 A | 1/1979 | Bunke ...................... 416/70 R |
| 4,153,685 A | 5/1979 | Serfontein ................... 424/94 |
| 4,160,505 A | 7/1979 | Rauschenberger .......... 206/571 |
| 4,226,328 A | 10/1980 | Beddow ..................... 206/364 |
| 4,282,316 A | 8/1981 | Modrovich .................. 435/12 |
| 4,293,074 A | 10/1981 | Dunsky ...................... 206/574 |
| D266,434 S | 10/1982 | Kowalski ..................... D19/35 |
| D271,370 S | 11/1983 | San Antonio ................. D8/14 |
| 4,620,548 A | 11/1986 | Hasselbrack ................ 128/758 |
| 4,641,662 A | 2/1987 | Jaicks ........................ 128/757 |
| D288,717 S | 3/1987 | Willich et al. ............... D24/17 |
| 4,736,850 A | 4/1988 | Bowman et al. ............ 206/570 |
| 4,748,113 A | 5/1988 | Marshall ...................... 435/12 |
| 4,777,947 A | 10/1988 | Zwick ........................ 128/304 |
| 4,803,983 A | 2/1989 | Siegel ........................ 128/321 |
| D301,371 S | 5/1989 | Kaprelian .................... D24/10 |
| 4,829,006 A | 5/1989 | Smith et al. ................. 435/301 |

(List continued on next page.)

FOREIGN PATENT DOCUMENTS

| | | |
|---|---|---|
| DE | 867426 | 2/1953 |
| EP | 0018825 | 2/1985 |
| EP | 0365459 A1 | 4/1990 |
| EP | 369292 | 5/1990 |

(List continued on next page.)

OTHER PUBLICATIONS

Abstract EP 07211898 A1, Neumeyer E S, Jul. 17, 1996.
Roda, A. et al., "Development of a Chemiluminescent Urease Activity Assay for Helicobacter pylori Infection Diagnosis in Gastric Mucosa Biopsies", *Analytical Biochemistry* 264, 1998, pp. 47–52.

(List continued on next page.)

*Primary Examiner*—David A. Redding
(74) *Attorney, Agent, or Firm*—William W. Letson; Nancy M. Klembus

(57) ABSTRACT

A diagnostic system may include a carrier having at least one well, an upper surface, and a cavity extending downwardly from the upper surface. A specimen-handling tool may be configured to be positioned within the cavity and may include an elongated body having a longitudinal axis that extends along the length of the elongated body, a first end comprising an outermost portion adapted to skewer a tissue biopsy specimen.

7 Claims, 8 Drawing Sheets

U.S. PATENT DOCUMENTS

| Patent No. | | Date | Inventor | Class |
|---|---|---|---|---|
| 4,923,801 | A | 5/1990 | Marshall et al. | 435/12 |
| 4,932,957 | A | 6/1990 | Zwick | 606/160 |
| 4,955,971 | A | 9/1990 | Goulter | 294/7 |
| 5,116,346 | A | 5/1992 | Yeh | 606/131 |
| D327,322 | S | 6/1992 | Brewer, Jr. | D24/147 |
| D328,347 | S | 7/1992 | Santora | D24/133 |
| 5,149,506 | A | 9/1992 | Skiba et al. | 422/102 |
| D331,800 | S | 12/1992 | Han | D24/143 |
| 5,182,191 | A | 1/1993 | Fan et al. | 435/7.9 |
| 5,228,201 | A | 7/1993 | Atkins | 30/332 |
| 5,238,651 | A | 8/1993 | Chuba | 422/61 |
| 5,256,684 | A | 10/1993 | Marshall | 514/398 |
| 5,258,178 | A | 11/1993 | Cordle et al. | 424/85.8 |
| 5,260,057 | A | 11/1993 | Cordle et al. | 424/85.8 |
| 5,304,540 | A | 4/1994 | Blackburn et al. | 514/2 |
| 5,314,804 | A | 5/1994 | Boguslaski et al. | 435/12 |
| 5,339,955 | A | 8/1994 | Horan et al. | 206/370 |
| 5,348,023 | A | 9/1994 | McLucas | 128/757 |
| 5,380,492 | A | 1/1995 | Seymour | 422/101 |
| 5,420,016 | A | 5/1995 | Boguslaski et al. | 435/12 |
| 5,431,884 | A | 7/1995 | McDonough et al. | 422/101 |
| 5,439,801 | A | 8/1995 | Jackson | 435/12 |
| 5,449,071 | A | 9/1995 | Levy | 206/569 |
| 5,479,019 | A | 12/1995 | Gross | 250/345 |
| 5,494,162 | A | 2/1996 | Treace et al. | 206/438 |
| 5,498,528 | A | 3/1996 | King | 435/34 |
| 5,501,597 | A | 3/1996 | Wilson | 433/141 |
| D368,520 | S | 4/1996 | Brewer, Jr. | D24/147 |
| 5,593,851 | A | 1/1997 | Jackson | 435/12 |
| 5,601,848 | A | 2/1997 | Marshall | |
| 5,624,554 | A | 4/1997 | Faulkner et al. | 210/232 |
| 5,668,011 | A | 9/1997 | Jackson | 435/309.1 |
| 5,679,570 | A | 10/1997 | Heckenmuller et al. | 435/287.9 |
| 5,682,665 | A | 11/1997 | Svanberg | 29/458 |
| 5,702,911 | A | 12/1997 | Whalen | 435/12 |
| 5,709,838 | A | 1/1998 | Porter et al. | 422/61 |
| D390,659 | S | 2/1998 | Chan et al. | D24/133 |
| 5,722,422 | A | 3/1998 | Palmer et al. | |
| D393,312 | S | 4/1998 | Huttner | D24/147 |
| 5,738,110 | A | 4/1998 | Beal et al. | 128/769 |
| 5,782,951 | A | 7/1998 | Aylen et al. | 71/28 |
| 5,846,488 | A | 12/1998 | Richardson | 422/61 |
| 5,846,751 | A | 12/1998 | Pronovost et al. | 435/232 |
| 5,854,013 | A | 12/1998 | Ollar et al. | 435/34 |
| 5,893,853 | A | 4/1999 | Arnold | 606/133 |
| D415,275 | S | 10/1999 | Huttner | D24/147 |
| 5,989,840 | A | 11/1999 | D'Angelo et al. | 435/7.32 |
| 5,997,567 | A | 12/1999 | Cangelosi | 606/210 |
| D419,238 | S | 1/2000 | Maissami | D24/152 |
| D420,133 | S | 2/2000 | Huttner | D24/147 |
| 6,039,959 | A | 3/2000 | Burnie | 424/234.1 |
| D423,669 | S | 4/2000 | Huttner et al. | D24/147 |
| 6,048,735 | A | 4/2000 | Hessel et al. | 436/518 |
| 6,060,241 | A | 5/2000 | Corthésy-Theulaz | 435/6 |
| 6,068,985 | A | 5/2000 | Cripps et al. | 435/7.32 |
| D428,489 | S | 7/2000 | Huttner et al. | D24/147 |
| D428,991 | S | 8/2000 | Fourie et al. | D24/147 |
| 6,113,875 | A | 9/2000 | Nyström et al. | 424/1.29 |
| 6,116,426 | A | 9/2000 | Slonim | 206/570 |
| D435,293 | S | 12/2000 | Tang | D24/152 |
| 6,156,346 | A | 12/2000 | Chen et al. | 424/9 |
| 6,165,736 | A | 12/2000 | Fawcett | |
| 6,171,811 | B1 | 1/2001 | Becerro De Bengoa Vallejo | |
| 6,172,215 | B1 | 1/2001 | Keshi et al. | |
| 6,187,556 | B1 | 2/2001 | Lee et al. | |
| D438,979 | S | 3/2001 | Gomes et al. | D24/216 |
| 6,228,605 | B1 | 5/2001 | Marshall | 435/34 |
| D445,503 | S | 7/2001 | Huttner | D24/146 |
| D447,237 | S | 8/2001 | Huttner et al. | D24/147 |
| 6,270,514 | B1 | 8/2001 | McDonald | 606/210 |
| 6,291,234 | B1 | 9/2001 | Raz et al. | |
| 6,309,818 | B1 | 10/2001 | Malinda et al. | 435/4 |
| D452,936 | S | 1/2002 | Grisoni | D28/55 |

FOREIGN PATENT DOCUMENTS

| | | |
|---|---|---|
| EP | 0606651 A2 | 7/1994 |
| EP | 0721898 A1 | 7/1996 |
| EP | 0896547 B1 | 6/2002 |
| FR | 2442268 | 7/1980 |
| FR | 2654436 | 5/1991 |
| GB | 1112251 | 5/1968 |
| GB | 1478742 | 7/1977 |
| GB | 2 037 811 | 7/1980 |
| JP | 58077663 A | 5/1983 |
| WO | 82/01646 | 5/1982 |
| WO | 89/09407 | 10/1989 |
| WO | 94/22380 | 10/1994 |
| WO | 98/54563 | 12/1998 |
| WO | 99/02101 | 1/1999 |
| WO | 99/25251 | 5/1999 |
| WO | 99/51769 | 10/1999 |
| WO | 99/61892 | 12/1999 |
| WO | 00/47710 A1 | 8/2000 |
| WO | WO 01/64543 | 9/2001 |

OTHER PUBLICATIONS

U.S. patent application Ser. No. 09/977,555, Marshall et al., filed Oct. 15, 2001, Method for the Detection of Urease and Method for Using Same.

U.S. patent application Ser. No. 09/977,556, Marshall et al., filed Oct. 15, 2001, System for the Detectio of Urease adn Method for Using Same.

U.S. patent application Ser. No. 10/026,321, Marshall et al., filed Dec. 20, 2001, Gel–Based Media for Transfer slides, Methods of Producing and Using same.

U.S. patent application Ser. No. 09/977,874, Marshall et al., filed Oct. 15,2001, Composition for the Detection of Gastrointestinal Disorders.

U.S. patent application Ser. No. 09/977,546, Marshall et al., filed Oct. 15, 2001, Systems for Performing Multiple Diagnostic Tests.

U.S. patent application Ser. No. 09/977,539, McMichael et al., filed Oct. 15, 2001, Methods for Performing Multiple Diagnostic Tests.

U.S. patent application Ser. No. 29/149,655, Peterson et al., filed Oct. 15, 2001, Separable Diagnostic Test System.

U.S. patent application Ser. No. 29/149,695, Peterson et al., filed Sep. 15, 2001, Separable Diagnostic Test Carrier.

U.S. patent application Ser. No. 29/149,657, Peterson et al., filed Oct. 15, 2001, Separable Test Carrier.

U.S. patent application Ser. No. 09/977,547, Peterson et al., filed Oct. 15, 2001, Systems for Diagnostic Testing.

U.S. patent application Ser. No. 29/149,653, McMichael et al., filed Oct. 15, 2001, Diagnostic Testing System.

U.S. patent application Ser. No. 29/149,654, McMichael et al., filed Oct. 15, 2001, Diagnostic Test Carrier.

U.S. patent application Ser. No. 29/149,656, McMichael et al., Oct. 15, 2001, Specimen–Handling Tool.

U.S. patent application Ser. No. 09/977,667, Marshall et al., filed Oct. 15, 2001, Diagnostic Testing System and Method for Detecting Helicobacter Pylori.

U.S. patent application Ser. No. 29/152,423, Peterson et al., filed Dec. 17, 2001, Diagnostic Test Kit.

U.S. patent application Ser. No. 29/152,428, Peterson et al., filed Dec. 17, 2001, Diagnostic Test Kit with Specimen–Handling Tool.

U.S. patent application Ser. No. 29/152,422, Peterson et al., filed Dec. 17, 2001, Two–Well Diagnostic Test Kit with Specimen–Handling Tool.

U.S. patent application Ser. No. 29/152,444, Peterson et al., filed Dec. 17, 2001, Specimen–Handling Tool.

U.S. patent application Ser. No. 29/152,429, Peterson et al., filed Dec. 17, 2001, Test Kit Specimen–Handling Tool.

U.S. patent application Ser. No. 29/152,430, Peterson et al., filed Dec. 17, 2001, Tool for Handling a Specimen.

CARRIER AND SPECIMEN-HANDLING TOOL FOR USE IN DIAGNOSTIC TESTING

The present invention relates generally to specimen-handling tools and carriers for use in diagnostic testing.

In the medical arena, diagnostic testing is frequently performed to determine if a particular medical condition is present in a given patient. Diagnostic testing systems, which may be referred to as test kits, are manufactured to test for a wide variety of conditions in numerous types of biological test specimens, such as, for example, blood, tissue biopsies, and saliva. Such testing systems may be utilized to determine the presence of particular bacteria, such as *Helicobacter pylori*. Some tests that have been proposed to detect *Helicobacter pylori* include those that are disclosed in numerous U.S. Patents, including, for example, U.S. Pat. No. 4,748,113 to Marshall, U.S. Pat. No. 5,314,804 to Boguslaski et al., U.S. Pat. No. 5,439,801 to Jackson, U.S. Pat. No. 5,702,911 to Whalen, U.S. Pat. No. 5,989,840 to D'Angelo et al., U.S. Pat. No. 6,068,985 to Cripps et al., U.S. Pat. No. 6,156,346 to Chen et al., and U.S. Pat. No. 6,187,556 to Lee et al., each of such patents being incorporated in their entirety by reference herein.

Particular embodiments of the present invention relate to a specimen-handling tool for use with a diagnostic test kit that includes an elongated body having a longitudinal axis that extends along the length of the elongated body, a first end and a second end. The first end may include an outermost portion that is adapted to manipulate a tissue biopsy specimen. The outermost portion may be formed as a truncated crescent so that the tip of the truncated crescent is not aligned with the longitudinal axis of the elongated body. The first end may also include an upper surface and a lower surface that is generally inclined toward the upper surface. The upper surface may be generally inclined toward the lower surface in selected embodiments.

The second end of the specimen-handling tool may include a curved upper surface. The specimen-handling tool may also include a gripping portion that may be disposed between the first end and the second end, and the gripping portion may include at least one rib.

The specimen-handling tool may include, in selected embodiments, an elongated body having a longitudinal axis that extends along the length of the elongated body, a first end and a second end. The first end may include an outermost portion, an upper surface, and a lower surface, the upper surface being generally inclined toward the lower surface, the outermost portion being formed as a truncated crescent. The second end may include a concavely curved upper surface.

A gripping portion may be positioned between the first end and the second end of the elongated body, and the gripping portion may include at least one rib. The elongated body may be roughly cylindrical in shape.

The present invention also relates to a diagnostic system that includes a carrier having at least one well, an upper surface, and a cavity extending downwardly from the upper surface. A specimen-handling tool may be configured to be positioned within the cavity and may include an elongated body having a longitudinal axis that extends along the length of the elongated body, a first end comprising an outermost portion adapted to manipulate a tissue biopsy specimen. The carrier may have at least two wells, and one of the wells of the carrier may be D-shaped. The specimen-handling tool and/or carrier may be formed of a rigid plastic such as, for example, polycarbonate.

Figure 1:
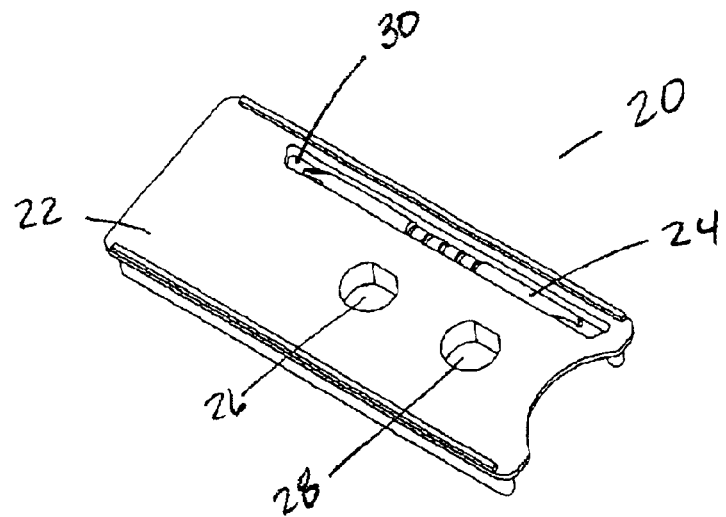
FIG. 1 is a perspective view of an embodiment of the system of the present invention.

FIG. 1 discloses an embodiment of a diagnostic system 20 according to the present invention that may be utilized for many types of diagnostic testing. Such diagnostic tests utilize a biological test specimen such as, for example, tissue biopsy, blood or saliva. The diagnostic system 20 may include a carrier 22 and a mechanism by which a user may manipulate a sample of tissue, such as, for example, the specimen-handling tool 24 that is shown in FIGS. 1 and 6–18.

Figure 2:
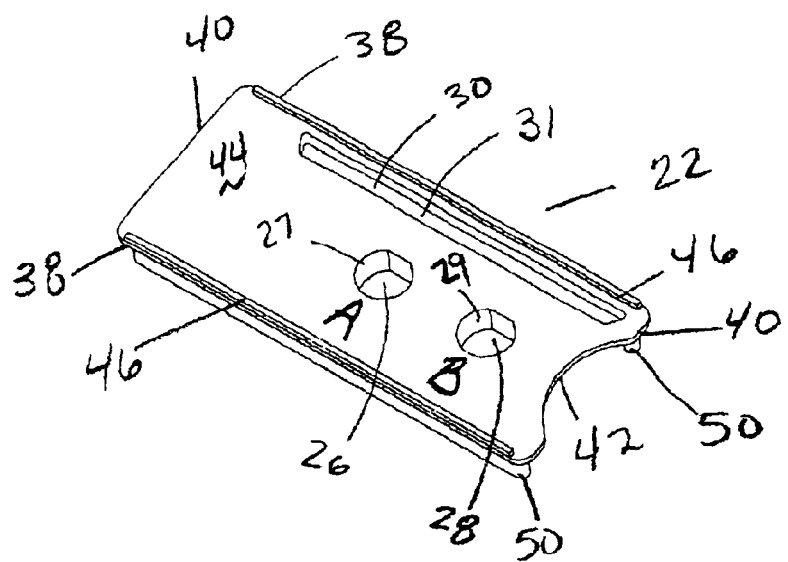
FIG. 2 is a perspective view of an embodiment of the carrier of the present invention.
Figure 3:
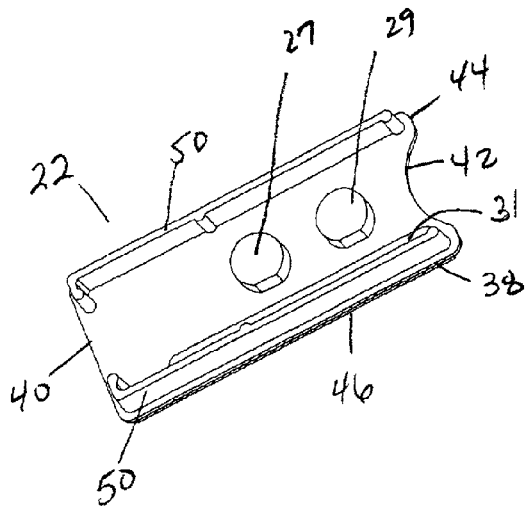
FIG. 3 is a perspective view of the bottom of an embodiment of the carrier of the present invention.
Figure 4:
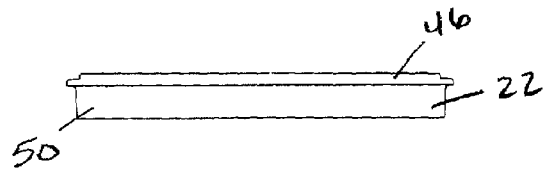
FIG. 4 is a side view of an embodiment of the carrier of the present invention.
Figure 5:
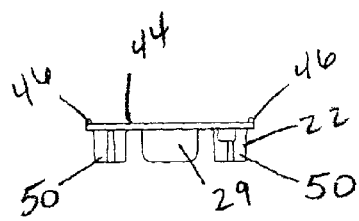
FIG. 5 is an end view of an embodiment of the carrier of the present invention.
Figure 6:
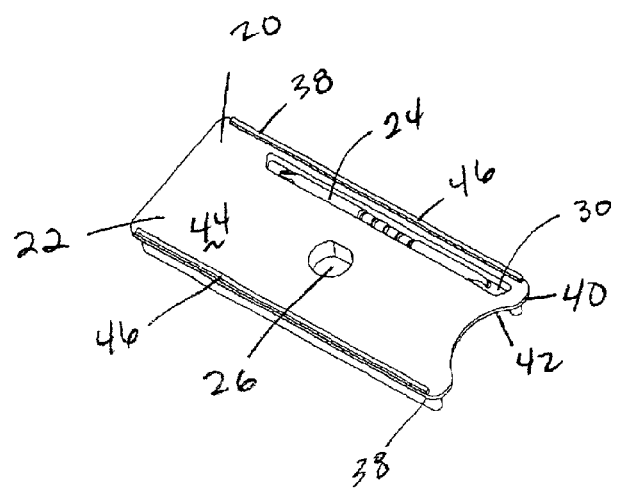
FIG. 6 is a perspective view of another embodiment of the system of the present invention.

As shown in FIGS. 1–3, the carrier 22 may include a first well 26 and a second well 28. As shown in FIG. 6, selected embodiments of the carrier 22 may include a single well 26. The wells 26 and 28 may be defined, at least in part, by the walls 27 and 29, respectively. The wells 26 and 28 may be formed to have a variety of different configurations, such as, for example, frustoconical, cylindrical, or other configurations. As shown in FIGS. 1–3, the wells 26 and/or 28, when viewed from the top of the carrier 22, are generally D-shaped. The wells 26 and/or 28 may be formed so that, when viewed from the top of the carrier 22, the wells 26 and/or 28 have any of a variety of shapes, such as, for example, elliptical, square, rectangular, or circular. The wells 26 and 28 of the carrier 22 may have similar configurations or dissimilar configurations.

The carrier 22 may have many different overall exterior shapes, such as, for example, the generally rectangular shape as shown in FIGS. 1–4 and 6. The carrier 22 may be alternately shaped, such as, for example, square, oblong, triangular, and the like. The carrier 22 may, as shown in FIGS. 2, 3 and 6, include two elongated sides 38, two ends 40 and a surface 44. The ends 40 may be configured to be easily grasped by a user and one, none or both of the ends 40 may include an arcuate portion 42 as shown in FIGS. 1, 2, 3 and 6.

As shown in FIGS. 1, 2, 5 and 6, the carrier 22 may include a surface 44. The first and/or second wells 26 and 28, respectively, may be configured to extend downwardly from the surface 44. As shown in FIGS. 1 and 2, the carrier 22 may also include a cavity 30. At least a portion of the cavity 30 may be formed by the wall 31. The cavity 30 may be configured to extend downwardly from the surface 44, as shown in FIGS. 1, 2, 3 and 6. In other embodiments, one or both of the wells 26 and 28 and/or the cavity 30 may be formed so as to extend upwardly from at least a portion of the surface 44.

A mechanism by which a user may manipulate a sample of tissue, such as, for example, the specimen handling tool 24 such as that shown in FIGS. 1 and 6–18, may also be included in particular embodiments of the diagnostic system 20 of the present invention. The specimen-handling tool 24 may be disposed within the cavity 30. In particular embodiments, the specimen-handling tool 24 may be removably attached to the carrier 22 by one or more locking arms, adhesive, or the like.

As shown in FIGS. 2–6, one or more rails 46 may be included in selected embodiments of the present invention and may be disposed on the carrier 22 so that the rails extend upwardly along at least a portion of the surface 44. In some embodiments, one or more rails 46 may also be configured to extend outwardly from the carrier 22.

As shown in FIGS. 2–6, one or more supports 50 may be provided which extend downwardly from the surface 44. As seen in FIG. 3, the supports 50 permit the carrier 22 to rest in a stable position on a horizontal or other surface. The rails 46 and the supports 50 may be configured to enable the carrier 22 to be automatically processed through a variety of equipment.

If desired, the surface 44 may be configured so that various indicia, such as letters, numbers, symbols and other characters, may be placed onto or formed into the surface 44. For example, and as shown in FIG. 2, each well 26 and/or 28 may be given a particular designation, such as A or B, and that designation may be printed or otherwise positioned upon the surface 44.

The carrier 22 may be formed from a variety of materials, including, for example, polycarbonate, polystyrene, polypropylene, polyethylene, polyvinylchloride, or any other type of polyolefin.

Particular embodiments of the specimen-handling tool 24 are shown in FIGS. 1, 6, and 7–18. The specimen-handling tool 24 may be configured to assist the user in accomplishing particular tasks, such as, for example, manipulating a specimen. The specimen-handling tool 24 may, in some embodiments and as shown in FIGS. 7–18, include a first end 58 and a second end 60 disposed at opposing ends of an elongated body 62 is disposed between the first end 58 and the second end 60. A longitudinal axis, as shown in FIG. 10, may extend along the length of the elongated body 62.

A gripping portion 64 may be provided along at least a portion of the body 62 to enhance the grippability of the specimen-handling tool 24. The gripping portion 64 may include one or more ribs 54, as seen in FIGS. 9 and 10.

Figure 7:
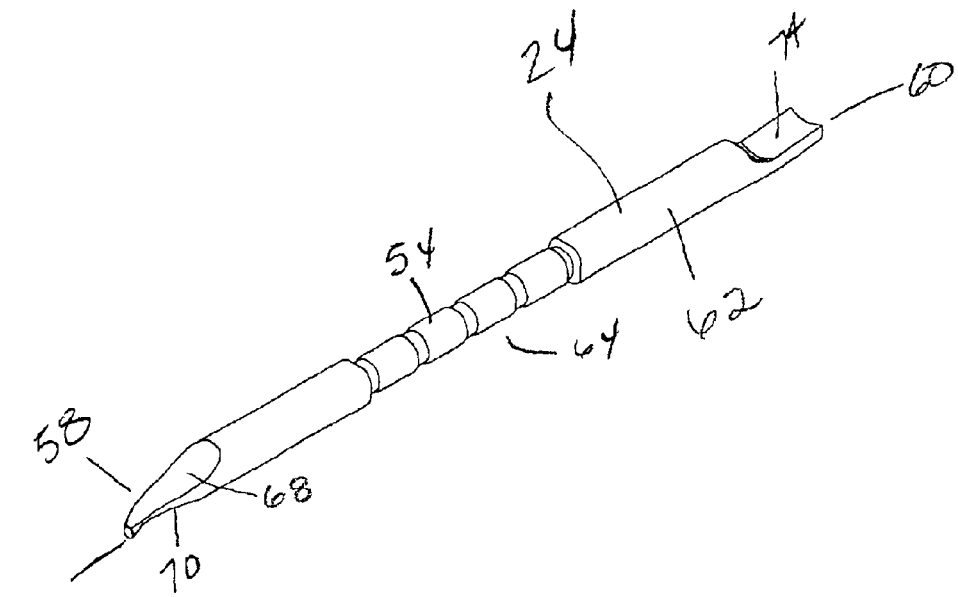
FIG. 7 is a perspective view of an embodiment of the specimen-handling tool of the present invention.
Figure 11:
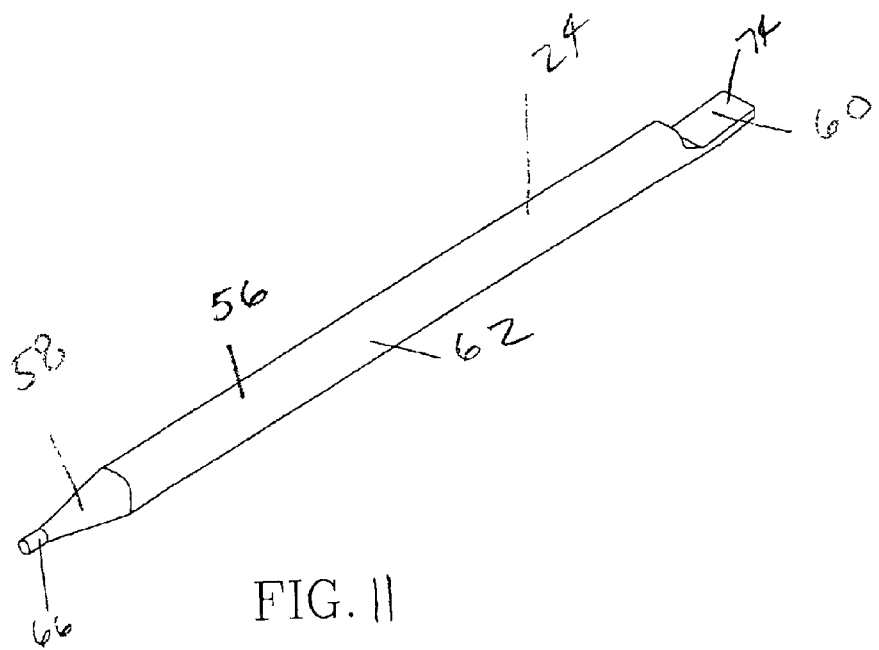
FIG. 11 is a perspective view of another embodiment of the specimen-handling tool of the present invention.
Figure 12:
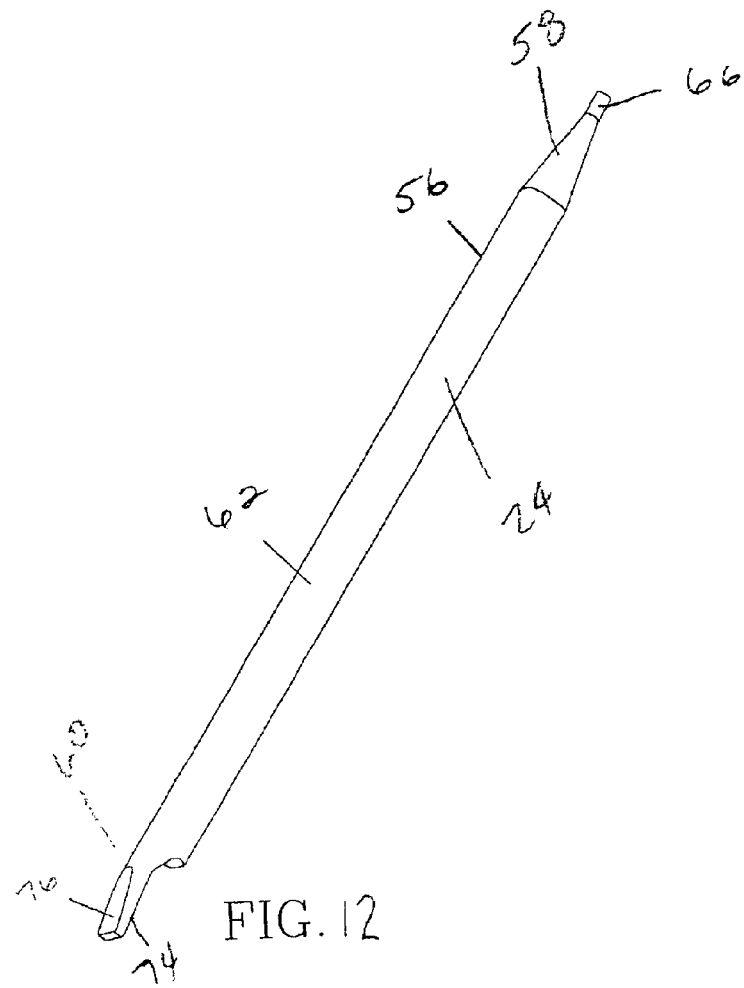
FIG. 12 is another perspective view of the embodiment of the specimen-handling tool depicted in FIG. 11.
Figure 13:
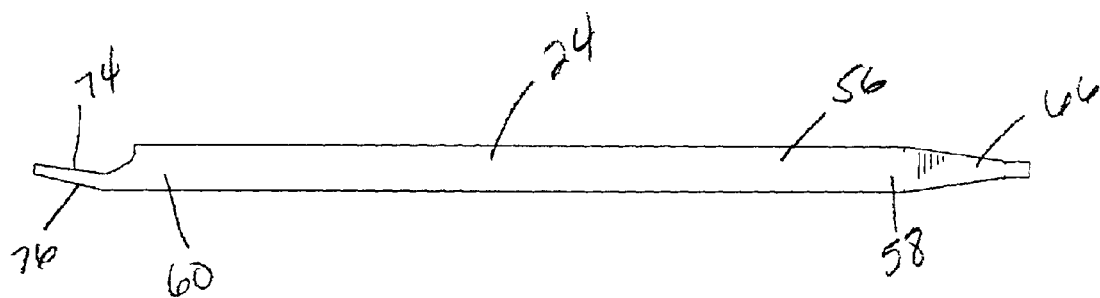
FIG. 13 is side view of the embodiment of the specimen-handling tool depicted in FIG. 11.
Figure 14:
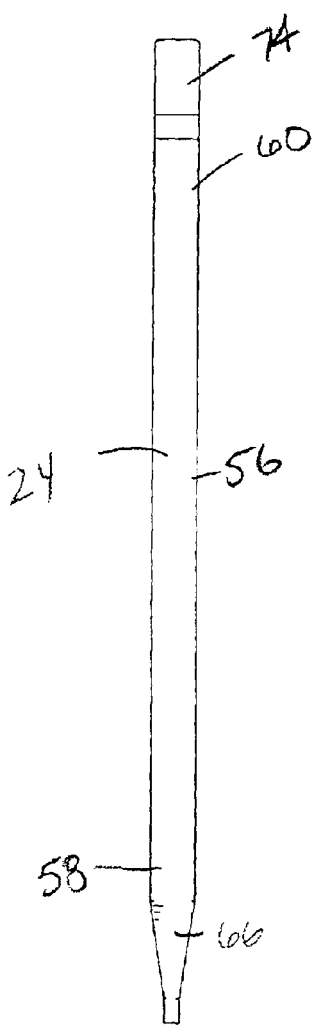
FIG. 14 is top view of the embodiment of the specimen-handling tool depicted in FIG. 11.
Figure 15:
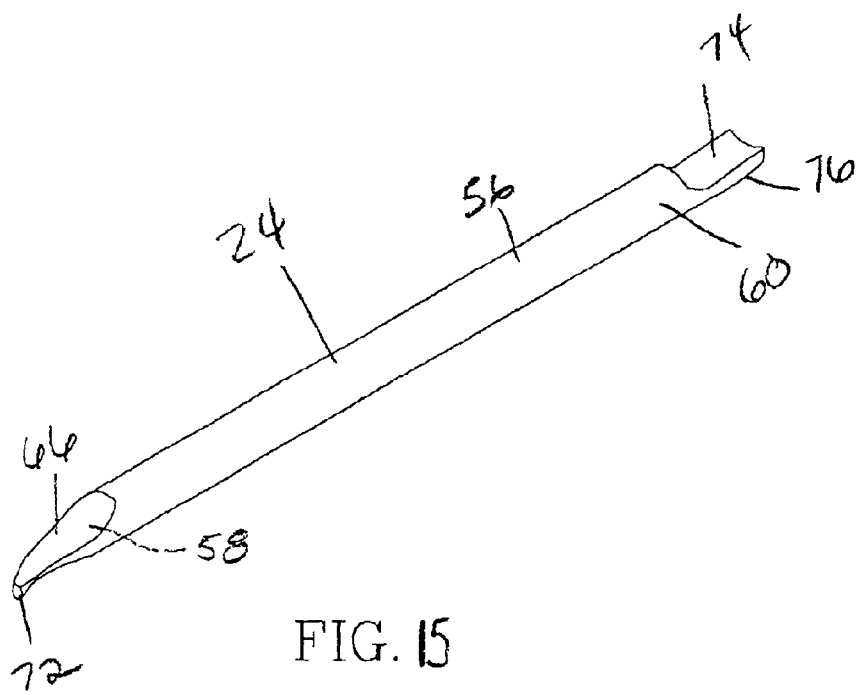
FIG. 15 is a perspective view of yet another embodiment of the specimen-handling tool of the present invention.

The first end 58 of the specimen-handling tool 24 is adapted to be at least partially inserted into or manipulate a tissue biopsy specimen. The outermost portion 66 of the first end 58 may be pointed, as shown in FIGS. 7, 11 and 15.

Figure 16:
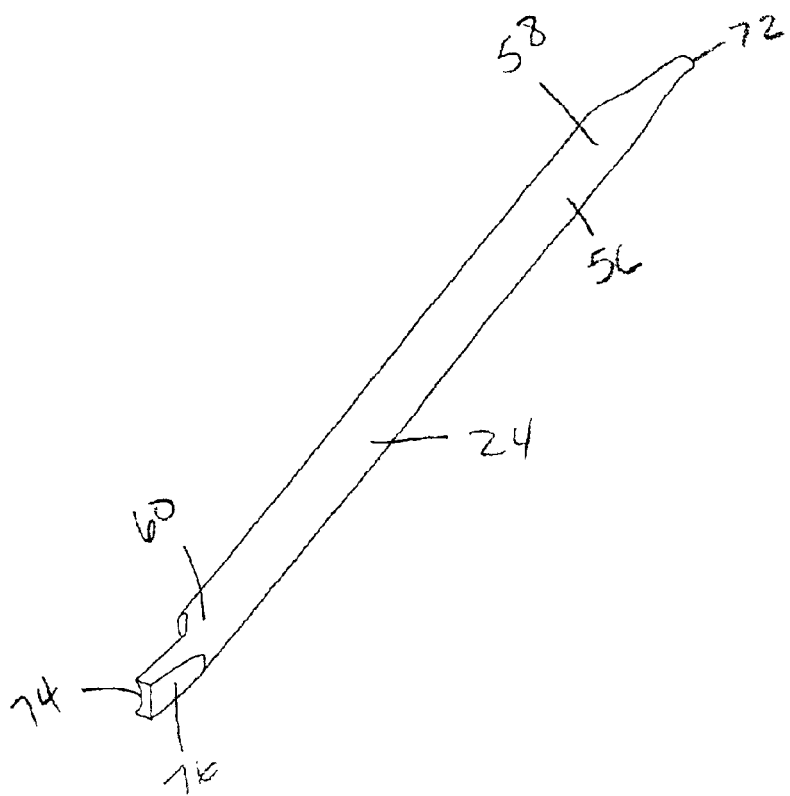
FIG. 16 is another perspective view of the embodiment of the specimen-handling tool depicted in FIG. 15.
Figure 17:
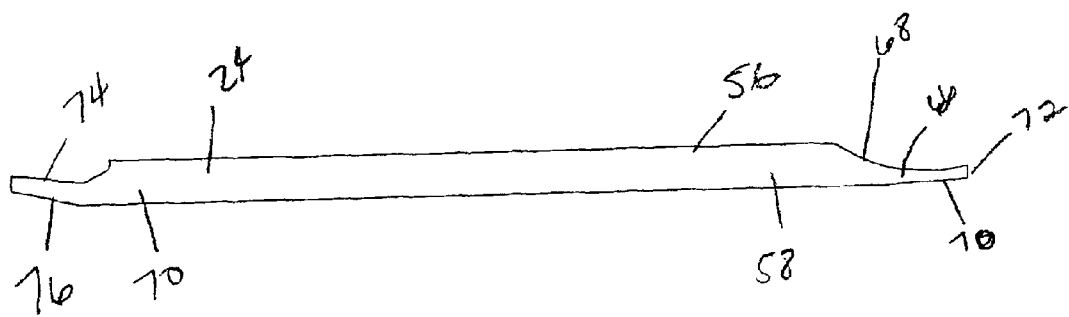
FIG. 17 is side view of the embodiment of the specimen-handling tool depicted in FIG. 15.
Figure 18:
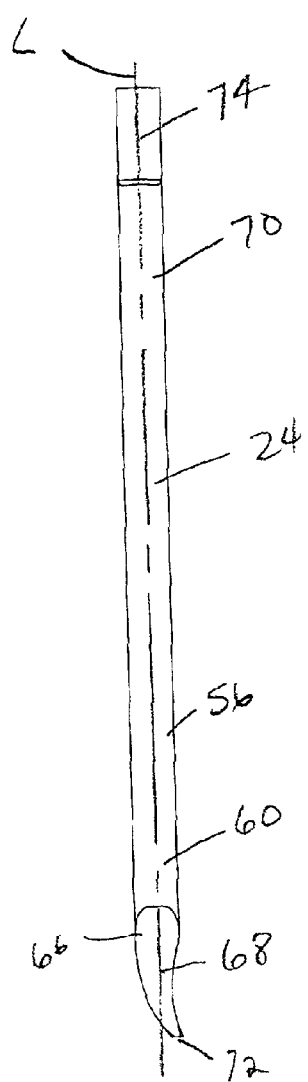
FIG. 18 is top view of the embodiment of the specimen-handling tool depicted in FIG. 15.

As shown in FIGS. 7–10 and 15–18, the outermost portion 66 may be formed as a crescent that extends outwardly from the first end 58. The crescent-shape of the outermost portion 66 results in the tip 72 of the outermost portion being spaced-apart from the longitudinal axis L of the elongated body 62 (see FIGS. 10 and 18). The tip 72 of the outermost portion 66 may be slightly truncated, as seen in FIGS. 10 and 18. In other embodiments and as shown in FIGS. 11–14, the outermost portion 66 may be otherwise formed.

Figure 8:
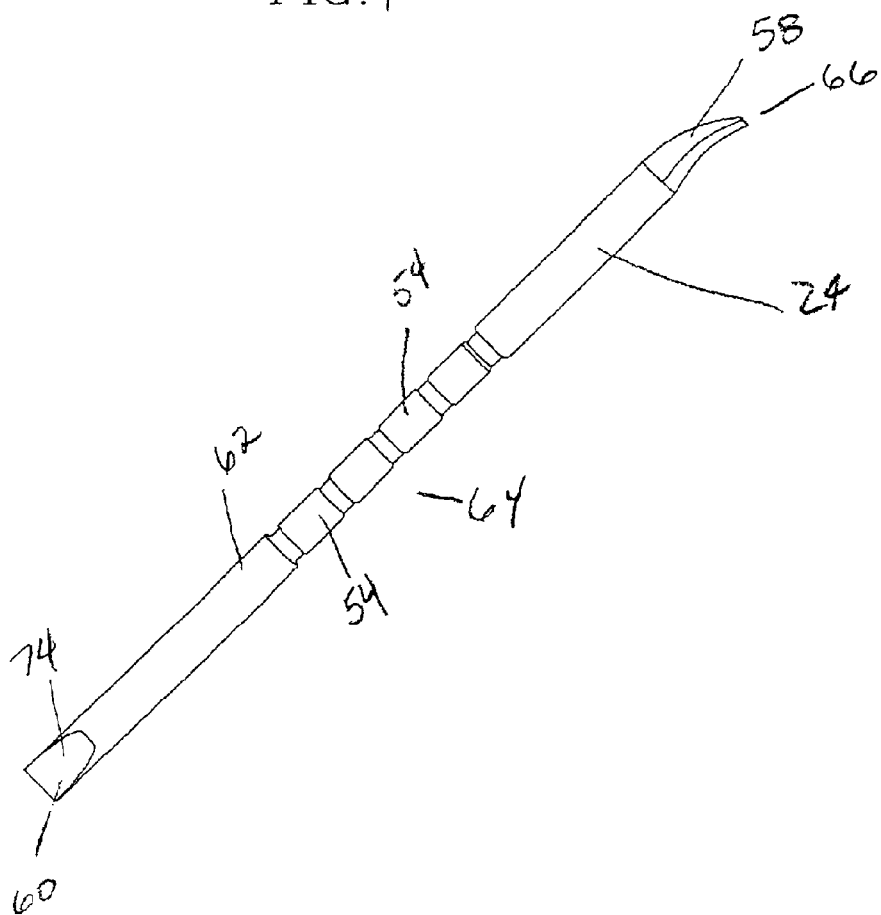
FIG. 8 is another perspective view of the embodiment of the specimen-handling tool depicted in FIG. 7.
Figure 9:
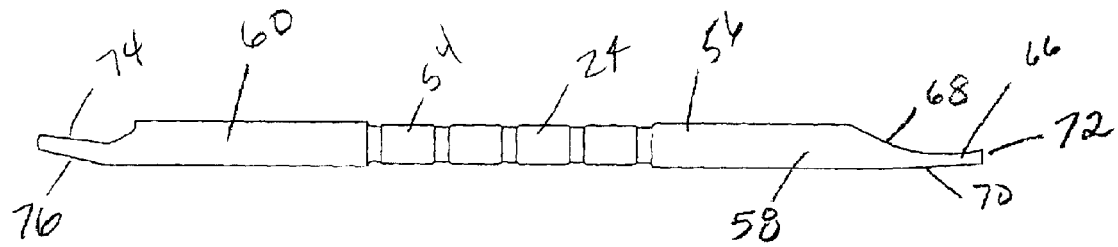
FIG. 9 is side view of the embodiment of the specimen-handling tool depicted in FIG. 7.
Figure 10:
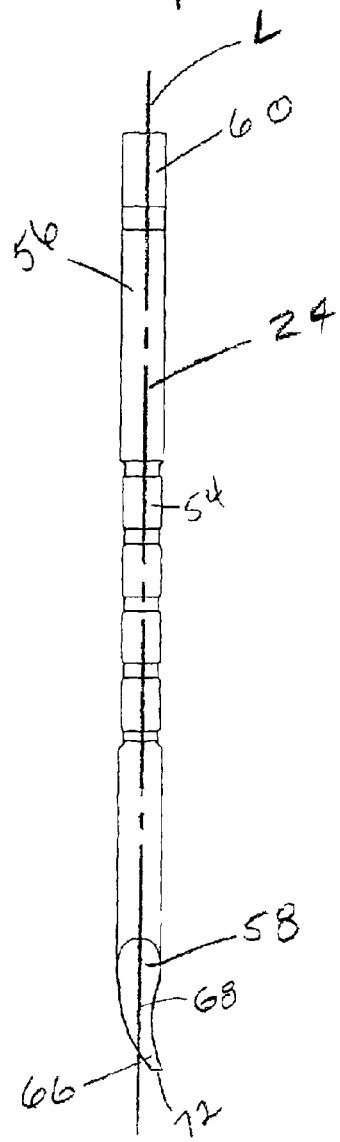
FIG. 10 is top view of the embodiment of the specimen-handling tool depicted in FIG. 7.

As seen in FIGS. 9 and 17, the first end 58 may also include an upper surface 68 and a lower surface 70. The upper surface 68 of the first end 58 may be generally inclined toward the lower surface 70. In some embodiments, the upper surface 68 may be arcuate (as shown in FIGS. 7 and 8) but the upper surface 68 may also be otherwise configured. The lower surface 70 may also be generally inclined toward the upper surface 68. The lower surface 70 and the upper surface 68 of the outermost portion 66 may be formed so that the outermost portion 66 has a uniform thickness (see FIG. 9) or a non-uniform thickness (see FIG. 11).

The second end 60 of the specimen-handling tool 24 may be used to support a tissue biopsy specimen. The second end 60 of the specimen-handling tool 24 may, as seen in FIGS. 7, 15 and 16, include an upper surface 74 that may, in some embodiments, be curved concavely. The second end 60 may also be formed into a spatula-type configuration where the upper surface 74 is approximately flat.

The specimen-handling tool may be formed from a variety of materials, including, for example, plastics including polycarbonate, polystyrene, polypropylene, polyethylene, polyvinylchloride, or any other type of polyolefin.

The invention may be embodied in other specific forms without departing from the scope and spirit of the inventive characteristics thereof. The present embodiments therefore are to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A specimen-handling tool for use with a diagnostic test kit comprising:
   an elongated body having a longitudinal axis that extends along the length of the elongated body;
   a first end; and
   a second end, the first end comprising an outermost portion adapted to skewer a tissue biopsy specimen, the outermost portion being formed as a truncated crescent so that the tip of the truncated crescent is not aligned with the longitudinal axis of the elongated body, the first end further comprising an upper surface and a lower surface that is generally inclined toward the upper surface, the upper surface being generally inclined toward the lower surface.

2. The specimen-handling tool as claimed in claim 1, the second end further comprising a curved upper surface.

3. The specimen-handling tool as claimed in claim 1 further comprising a gripping portion disposed between the first end and the second end, the gripping portion comprising at least one rib.

4. The specimen-handling tool as claimed in claim 1 being formed of a rigid plastic.

5. A specimen-handling tool comprising:
   an elongated body having a longitudinal axis that extends along the length of the elongated body;
   a first end comprising an outermost portion, an upper surface, and a lower surface, the upper surface being generally inclined toward the lower surface, the outermost portion being formed as a truncated crescent;

a second end comprising a concavely curved upper surface; and a gripping portion disposed between the first end and the second end, the gripping portion comprising at least one rib.

6. The specimen-handling tool as claimed in claim 5, the outermost portion further including a tip disposed at the end of the truncated crescent, the tip being spaced apart from the longitudinal axis of the elongated body.

7. The specimen-handling tool as claimed in claim 5 being formed of a rigid plastic.

* * * * *